United States Patent [19]

Sloan

[11] 4,206,220
[45] Jun. 3, 1980

[54] PRODRUGS FOR THE IMPROVED DELIVERY OF NON-STEROIDAL ANTI-INFLAMMATORY AGENTS

[75] Inventor: Kenneth B. Sloan, Eudora, Kans.

[73] Assignee: INTERx Research Corporation, Lawrence, Kans.

[21] Appl. No.: 924,303

[22] Filed: Jul. 13, 1978

[51] Int. Cl.$^2$ .................... A61K 31/40; C07D 209/18
[52] U.S. Cl. ........................... 424/274; 260/326.13 A
[58] Field of Search ............... 260/326.13 A; 424/274

[56] References Cited

PUBLICATIONS

Open Chain Nitrogen Compounds, Smith (1966) pp. 96–97 by W. A. Benjamin Inc., New York, Amsterdam. Chem. Abst, vol. 84, 43747a, (1976).

*Primary Examiner*—Stanley J. Friedman
*Attorney, Agent, or Firm*—Burns, Doane, Swecker & Mathis

[57] ABSTRACT

Novel prodrug forms of carboxylic acid, non-steroidal, anti-inflammatory agents are disclosed, having the structural formula

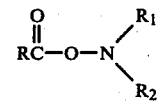

wherein

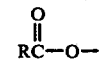

represents the acyloxy residue of any non-steroidal anti-inflammatory drug which contains a carboxylic acid function; $R_1$ and $R_2$, which can be the same or different, each represents a member selected from the group consisting of $C_1$–$C_8$ alkyl, $C_2$–$C_8$ alkenyl, aryl, aralkyl, $C_5$–$C_6$ cycloalkyl and $C_5$–$C_6$ cycloalkenyl; or $R_1$ and $R_2$ are combined so that —$NR_1R_2$ together form a member selected from the group consisting of a cycloheteroalkyl radical such as morpholino, 1-pyrrolidinyl, 4-methyl-1-piperazinyl or piperidino and a heteroaryl radical, such as 1-imidazolyl or 1-pyrazolyl; and the nontoxic pharmaceutically acceptable acid addition salts thereof.

These compounds exhibit oral and topical anti-inflammatory activity when administered to warmblooded animals and are characterized as being more readily bioavailable, less irritating to topical and gastric mucosal membranes and more permeable through topical membranes, e.g., ophthalmic membrane, skin, etc., than are the "parent" non-steroidal anti-inflammatory drugs from which they are derived.

11 Claims, No Drawings

PRODRUGS FOR THE IMPROVED DELIVERY OF NON-STEROIDAL ANTI-INFLAMMATORY AGENTS

BACKGROUND OF THE INVENTION

1. Field of the Invention:

The present invention relates to novel and useful derivatives of non-steroidal anti-inflammatory drugs containing a carboxylic acid function. In particular, the present invention relates to novel forms of these non-steroidal anti-inflammatory drugs characterized as being (1) more readily bioavailable; (2) less irritating to topical and gastric mucosal membranes; and (3) more permeable through topical membranes such as the ophthalmic membrane, skin, etc., when administered orally or topically to warm-blooded animals than are the non-steroidal anti-inflammatory drugs from which they are derived.

For the purposes of this specification, the term "prodrug" denotes a derivative of a known and proven prior art non-steroidal anti-inflammatory compound (e.g., indomethacin, aspirin, naproxen, etc.), which derivative, when administered to a warm-blooded animal, "cleaves" in such a manner as to release the proven drug form at its target site or sites of activity. The enzymatic and/or chemical hydrolytic "cleavage" of the compounds of the instant invention occurs in such a manner such that the proven drug form (the conventional non-steroidal anti-inflammatory agent) is released while the remaining "cleaved" moiety remains nontoxic and is metabolized in such a manner that nontoxic, metabolic products are produced.

2. Description of the Prior Art

Usually, the un-ionized form of a drug is absorbed more efficiently than its ionic species. In the case of non-steroidal anti-inflammatory drugs containing the carboxylic acid functional group such as indomethacin, aspirin, naproxen and the like, the carboxylic acid is significantly ionized at physiological pH. The result is that such non-steroidal anti-inflammatory drugs are poorly absorbed through lipid-water membrane barriers and are irritating. Thus, an object of the present invention is to provide a class of derivatives of non-steroidal anti-inflammatory drugs which would not be significantly ionized at physiological pH and which are reasonably stable but which hydrolyze readily in vivo.

The present derivatives of non-steroidal anti-inflammatory drugs are basic compounds, each compound being the acylate of a hydroxylamine; however, by virtue of the oxygen-nitrogen bond, the $pK_a$ of the amine is lowered to well below 7.0 so that, at physiological pHs, the derivative is in its unionized form. In addition, the present derivatives of non-steroidal anti-inflammatory drugs are reasonably stable, reacting only slowly with highly nucleophilic amines in the absence of acid catalyst [B. O. Handford, T. H. Jones, G. T. Young and T. F. N. Johnson, J. Chem. Soc., 6814 (1965)] while it can be expected that in vivo such derivatives will be rapidly cleaved by esterases.

The result of the hydrolysis of the novel prodrug derivatives of the present invention yields the known anti-inflammatory drug and one molecule of an N-hydroxydialkylamine or similar N-hydroxydi(substituted)amine. N-oxidation of dialkylamines is one of the metabolic pathways for elimination of dialkylamines and there appears to be an equilibrium between the dialkylamine and its N-oxidized form which is reduced pyridine nucleotide-dependent. [F. F. Kadlubar, E. M. McKee, D. M. Ziegler, Arch. Biochem. Biophys., 156, 46 (1973)] Thus, the N-hydroxydialkylamine is comparable in toxicity to the dialkylamine from which it is derived.

The derivatives of the non-steroidal anti-inflammatory drugs of the present invention therefore provide more easily absorbed and less irritating forms of the un-ionized state of the drug. In addition, the hydrolysis of the derivatives of the present invention yield only the parent non-steroidal anti-inflammatory drug and a nontoxic N-hydroxyamine which is readily eliminated.

SUMMARY OF THE INVENTION

It is one object of the present invention to provide prodrug forms of conventional non-steroidal anti-inflammatory agents which exhibit oral and topical anti-inflammatory activity when administered to warm-blooded animals and are characterized as being more readily bioavailable, less irritating to topical and gastric mucosal membranes and more permeable through topical membranes, e.g., ophthalmic membrane, skin, etc. than are the non-steroidal anti-inflammatory drugs from which they are derived.

It is another object of the present invention to provide such prodrug forms of conventional anti-inflammatory compounds which, following administration, will "cleave" in such a manner as to enable the original parent moiety (e.g., indomethacin, aspirin, naproxen, etc.) to be released at its therapeutic site or sites of anti-inflammatory activity and to further permit the cleaved moiety(ies) unassociated with the parent moiety to be metabolized in a nontoxic fashion.

The foregoing objects are achieved by topically or orally administrating to a warm-blooded animal afflicted with inflammation, a therapeutically effective anti-inflammatory amount of a compound having the formula:

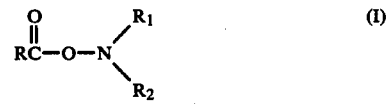

wherein

represents the acyloxy residue of any non-steroidal anti-inflammatory drug which contains a carboxylic acid function; $R_1$ and $R_2$, which can be the same or different, each represents a member selected from the group consisting of $C_1$-$C_8$ alkyl, $C_2$-$C_8$ alkenyl, aryl, aralkyl, $C_5$-$C_6$ cycloalkyl and $C_5$-$C_6$ cycloalkenyl; or $R_1$ and $R_2$ are combined so that —$NR_1R_2$ together form a member selected from the group consisting of a cycloheteroalkyl radical such as morpholino, 1-pyrrolidinyl, 4-methyl-1-piperazinyl or piperidino and a heteroaryl radical, such as 1-imidazolyl or 1-pyrazolyl; and the nontoxic pharmaceutically acceptable acid addition salts thereof.

The term "nontoxic pharmaceutically acceptable acid addition salt" as used herein generally includes the nontoxic acid addition salts of selected compounds of formula (I), formed with nontoxic inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, sulfonic, toluenesulfonic, and the like.

The chemical structure of the non-steroidal anti-inflammatory drugs whose residues are encompassed by formula (I) is not critical, so long as those drugs contain a carboxylic acid function. Suitable anti-inflammatory agents from which the instant prodrugs are derived include, but are not limited to, indomethacin, aspirin, naproxen, fenoprofen, sulindac, ibuprofen, tolmetin, difunisal, flurbiprofen, indoprofen, mefanamic acid, fenclozic acid, ketoprofen, alclofenac, bucloxic acid, meclofenamic acid, flufenamic acid, cinchophen, voltaren, cinmetacin, ibufenac, furobufen, fenclofenac, prodolic acid, pirprofen, oxoprozin, clonixin, fluprofen and flutiazin.

With respect to the radicals encompassed by $R_1$, $R_2$ and $-NR_1R_2$ in formula (I) and throughout this specification, the following definitions are applicable:

The term "cycloheteroalkyl" encompasses saturated monocyclic compounds containing one or more hetero atoms in the ring, optionally bearing one or more substituents such as phenyl, benzyl and methyl. Illustrative of such cycloheteroalkyl groups are morpholino, 1-pyrrolidinyl, 4-methyl-1-piperazinyl, piperidino, hexamethyleneimino, 4-phenylpiperidino, 4-benzylpiperidino and 4-phenyl-1-piperazinyl.

The term "aryl" encompasses unsubstituted aryl radicals such as phenyl and naphthyl and also the corresponding aryl radicals containing one or more substituents, which may be the same or different, such as alkylthio, alkyl, halo, alkoxy, nitro, alkanoyl, carbalkoxy, dialkylamino, alkanoyloxy, trifluoromethyl, alkylsulfonyl and cyano groups. Similarly, the term "heteroaryl" used here and throughout this specification encompasses unsubstituted radicals such as 1-imidazolyl, 1-pyrazolyl, 1-pyridyl, 1-quinolyl, 2-isoquinolyl, 1- or 3-pyrimidinyl and 1- or 4-pyrazinyl, as well as the corresponding radicals containing one or more methyl groups.

In addition, here and throughout this specification, the following definitions are applicable: The alkyl radicals contain 1 to 8 carbon atoms, e.g., methyl, ethyl, propyl, butyl, pentyl, hexyl, heptyl and octyl and the branched-chain isomers thereof. The alkenyl radicals contain 2 to 8 carbon atoms and may be straight or branched-chain, for example, vinyl, propenyl and the like. The cycloalkyl and cycloalkenyl radicals contain 5 or 6 carbon atoms, e.g., cyclopentyl, cyclohexyl and cyclopentenyl. The aralkyl radicals are of the type —alkylene—aryl wherein aryl is as defined above and the alkylene moiety contains 1 to 6 carbon atoms and can be straight or branched-chain, e.g., methylene, ethylene, propylene, trimethylene, 1,2-butylene, 2,3-butylene, tetramethylene and the like. Additionally, insofar as concerns the optional substituents encompassed by the definition of "aryl" above, the alkylthio, alkoxy, alkanoyl, carbalkoxy, dialkylamino, alkanoyloxy and alkylsulfonyl radicals are of the type

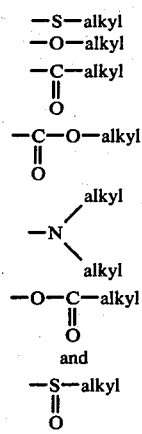

respectively, wherein "alkyl" is as hereinbefore defined.

DETAILED DESCRIPTION OF THE INVENTION

While all of the compounds encompassed by formula (I) above essentially satisfy the objections of the present invention, the following selected compounds are preferred:

1. N-[1-(4'-Chlorobenzoyl)-5-methoxy-2-methyl-3-indolylacetyloxy]-N,N-dimethylamine.
2. N-[1-(4'-Chlorobenzoyl)-5-methoxy-2-methyl-3-indolylacetyloxy]-N,N-diethylamine.
3. N-[1-(4'-Chlorobenzoyl)-5-methoxy-2-methyl-3-indolylacetyloxy]-N,N-dipentylamine.
4. N-[1-(4'-Chlorobenzoyl)-5-methoxy-2-methyl-3-indolylacetyloxy]-N,N-dioctylamine.
5. N-{cis-5-Fluoro-2-methyl-1-[4'-(methylsulfinyl)benzylidene]indene-3-acetyloxy}piperidine.
6. N-{cis-5-Fluoro-2-methyl-1-[4'-(methylsulfinyl)benzylidene]indene-3-acetyloxy}benzylaniline.
7. N-{cis-5-Fluoro-2-methyl-1-[4'-(methylsulfinyl)benzylidene]indene-3-acetyloxy}morpholine.
8. 1-{cis-5-Fluoro-2-methyl-1-[4'-(methylsulfinyl)benzylidene]indene-3-acetyloxy}imidazole.
9. N-[(+)-6-Methoxy-α-methyl-2-naphthaleneacetyloxy]-N,N-dimethylamine.
10. N-[(+)-6-Methoxy-α-methyl-2-naphthaleneacetyloxy]-N,N-diethylamine.
11. N-[(+)-6-Methoxy-α-methyl-2-naphthaleneacetyloxy]-N,N-dipentylamine.
12. N-[(+)-6-Methoxy-α-methyl-2-naphthaleneacetyloxy]-N,N-dioctylamine.
13. N-(α-Methyl-3-phenoxybenzeneacetyloxy)piperidine.
14. N-(α-Methyl-3-phenoxybenzeneacetyloxy)benzylaniline.
15. N-(α-Methyl-3-phenoxybenzeneacetyloxy)morpholine.
16. 1-(α-Methyl-3-phenoxybenzeneacetyloxy)imidazole.
17. N-[2-(Acetyloxy)benzoyloxy]-N,N-dimethylamine.
18. N-[2-(Acetyloxy)benzoyloxy]-N,N-diethylamine.
19. N-[2-(Acetyloxy)benzoyloxy]-N,N-dipentylamine.
20. N-[2-(Acetyloxy)benzoyloxy]-N,N-dioctylamine.
21. N-[α-Methyl-4-(2'-methylpropyl)benzeneacetyloxy]piperidine.
22. N-[α-Methyl-4-(2'-methylpropyl)benzeneacetyloxy]benzylaniline.

23. N-[α-Methyl-4-(2'-methylpropyl)benzeneacetyloxy]morpholine.
24. 1-[α-Methyl-4-(2'-methylpropyl)benzeneacetyloxy]imidazole.
25. N-[1-Methyl-5-(p-toluoyl)pyrrole-2-acetyloxy]-N,N-dimethylamine.
26. N-[1-Methyl-5-(p-toluoyl)pyrrole-2-acetyloxy]-N,N-diethylamine.
27. N-[1-Methyl-5-(p-toluoyl)pyrrole-2-acetyloxy]-N,N-dipentylamine.
28. N-[1-Methyl-5-(p-toluoyl)pyrrole-2-acetyloxy]-N,N-dioctylamine.
29. N-[2-Hydroxy-5-(2',4'-difluorophenyl)benzoyloxy]piperidine.
30. N-[2-Hydroxy-5-(2',4'-difluorophenyl)benzoyloxy]benzylaniline.
31. N-[2-Hydroxy-5-(2',4'-difluorophenyl)benzoyloxy]morpholine.
32. 1-[2-Hydroxy-5-(2',4'-difluorophenyl)benzoyloxy]imidazole.
33. N-(3-Fluoro-4-phenylhydratropoyloxy)-N,N-dimethylamine.
34. N-(3-Fluoro-4-phenylhydratropoyloxy)-N,N-diethylamine.
35. N-(3-Fluoro-4-phenylhydratropoyloxy)-N,N-dipentylamine.
36. N-(3-Fluoro-4-phenylhydratropoyloxy)-N,N-dioctylamine.
37. N-[4-(1'-Oxo-2'-isoindolinyl)hydratropoyloxy]piperidine.
38. N-[4-(1'-Oxo-2'-isoindolinyl)hydratropoyloxy]benzylaniline.
39. N-[4-(1'-Oxo-2'-isoindolinyl)hydratropoyloxy]morpholine.
40. 1-[4-(1'-Oxo-2'-isoindolinyl)hydratropoyloxy]imidazole.
41. N-{2-[2,3-Dimethylphenyl)amino]benzoyloxy}-N,N-dimethylamine.
42. N-{2-[2,3-Dimethylphenyl)amino]benzoyloxy}-N,N-diethylamine.
43. N-{2-[2,3-Dimethylphenyl)amino]benzoyloxy}-N,N-dipentylamine.
44. N-{2-[2,3-Dimethylphenyl)amino]benzoyloxy}-N,N-dioctylamine.
45. N-[(+)-6-Methoxy-α-methyl-2-naphthaleneacetyloxy]piperidine.
46. N-[1-(4'-Chlorobenzoyl)-5-methoxy-2-methyl-3-indolylacetyloxy]-piperidine.

It will be apparent to those skilled in the art that the preferred compounds listed above are derived from indomethacin, sulindac, naproxen, fenoprofen, aspirin, ibuprofen, tolmetin, diflunisal, flurbiprofen, indoprofen and mefenamic acid. Other suitable anti-inflammatory agents from which the instant prodrugs can be derived include, but are not limited to, fenclozic acid, ketoprofen, alclofenac, bucloxic acid, meclofenamic acid, flufenamic acid, cinchophen, voltaren, cinmetacin, ibufenac, furobufen, fenclofenac, prodolic acid, pirprofen, oxoprozin, clonixin, fluprofen and flutiazin.

The novel prodrugs of formula (I) can be prepared by allowing stoichiometric amounts of a non-steroidal anti-inflammatory agent of the formula

wherein

is as hereinbefore defined, to react with an N-hydroxylamine of the formula $$HO-N\begin{matrix}R_1\\R_2\end{matrix} \qquad (III)$$

wherein $R_1$ and $R_2$ are defined as before, in the presence of a suitable dehydrating agent, e.g., dicyclohexylcarbodiimide or N-ethoxycarbonyl-2-ethoxy-1,2-dihydroquinoline, in the presence of a conventional halogenated solvent, e.g., dichloromethane, dichloroethane or chloroform, or a conventional ether solvent, e.g., dioxane or tetrahydrofuran. The reaction is carried out over a period of one to twenty-four hours at standard temperature and pressure. Alternatively, the compounds of formula (I) can be prepared by allowing an equivalent amount of a compound of the formula

i.e., the acid chloride derivative of (II), to react with two equivalents of an N-hydroxylamine of formula (III) in a conventional halogenated or ether solvent as described above. Alternatively, the derivatives of formula (I) can be prepared by first allowing stoichiometric amounts of the non-steroidal anti-inflammatory carboxylic acid of formula (II) to react with an alkyl chloroformate and an acid scavenger such as triethylamine, in a conventional halogenated or ether solvent as described above, then with the N-hydroxylamine of formula (III). The final product can then be purified in each of the preceding cases by conventional means such as crystallization, distillation or chromatography.

Without further elaboration, it is believed that one of ordinary skill in the art can, using the preceding description, utilize the present invention to its fullest extent. Therefore, the following preferred specific embodiments are to be construed as merely illustrative and not limitative of the remainder of the specification and claims in any way whatsoever.

EXAMPLE 1

The Preparation of the Acid Chloride of 1-(4'-Chlorobenzoyl)-5-Methoxy-2-Methyl-3-Indolylacetic Acid, i.e., Indomethacin Acid Chloride (A)

To 9.00 g (0.0757 mol) of thionyl chloride in 400 ml of dichloromethane was added 5.55 g (0.076 mol) of dimethylformamide in 100 ml of dichloromethane. After 10 minutes at room temperature, the above solution was allowed to react with a dichloromethane (100 ml) suspension containing 25.7 g (0.072 mol) of indomethacin. The resulting faintly orange solution was immediately concentrated in vacuo to give a light yellow residue which was triturated with 500 ml of ether overnight. The precipitate was then filtered and dried to give 16.7 (mp 124°–126° C., 61% yield) of the desired indomethacin acid chloride (A): IR (KBr) 1790 and 1675 cm$^{-1}$ (s) (C=O); NMR (CDCl$_3$)δ7.60 (AB quartet, 4, J=9 Hz; Δ$\nu_{AB}$=11 Hz, aromatic ), 7.0–6.55 (m, 3, aromatic H), 4.17 (s, 2, CH$_2$COCl) 3.83 (s, 3, O—CH$_3$) and 2.41 (s, 3, CH$_3$—C=C).

Anal. Calcd for C$_{19}$H$_{15}$Cl$_2$NO$_3$: C, 60.65; H, 4.02; N, 3.72. Found: C, 60.59; H, 4.08; N, 3.50.

EXAMPLE 2

The Preparation of
N-[1-(4'-Chlorobenzoyl)-5-Methoxy-2-Methyl-3-Indolylacetyloxy]-N,N-Diethylamine (B)

To 8.3 g (0.022 mol) of indomethacin acid chloride (A) suspended in 200 ml of ether was added with stirring, an ether (50 ml) solution containing 3.90 g (0.044 mol) of N,N-diethylhydroxylamine. The suspension that resulted was filtered after 1 hour and the filtrate was concentrated in vacuo to give 9.0 g (mp 93.5°–97° C., 95% yield) of the desired compound as a light yellow solid. The crude solid was crystallized from 320 ml of warm ether to give 5.82 g (mp 95°–98° C., 61% yield) of analytically pure derivative (B): TLC (silica gel, ether) R$_f$ 0.37; IR (KBr) 1750 and 1675 (cm$^{-1}$) (s) (C=O); NMR (CDCl$_3$)$\delta$7.57 (AB quartet, b 4 J=9 Hz, $\Delta_{\nu AB}$=11 Hz, aromatic-H), 7.05–6.55 (m, 3, aromatic-H), 3.83 (s, 3, O—CH$_2$C=O), 2.9 (q, 4, J=7 Hz, CH$_3$CH$_2$N), 2.4 (s, 3, CH$_3$—C=O) and 1.05 (t, 6, CH$_3$CH$_2$N).

Anal. Calcd for C$_{23}$H$_{25}$ClN$_2$O$_4$: C, 64.40; H, 5.87; N, 6.53. Found: C, 64.50; H, 5.82; N, 6.20.

EXAMPLE 3

The Preparation of
N-[(+)-6-Methoxy-α-Methyl-2-Naphthaleneacetyloxy]piperidine (C)

To 1.15 g (0.005 mol) of (+)-6-methoxy-α-methyl-2-naphthaleneacetic acid, i.e., naproxen, in 50 ml of ethyl acetate was added 0.53 g (0.005 mol) of N-hydroxypiperidine in 20 ml of ethyl acetate and 1.1 g (0.005 mol) of dicyclohexylcarbodiimide. A suspension formed immediately. After 0.5 hour, the suspension was filtered and the residue of dicyclohexylurea (0.6 g) was discarded. The filtrate was concentrated and that residue was suspended in 200 ml of ether and filtered. The ether filtrate was concentrated and that residue was crystallized from 20 ml of cyclohexane. The crystals from cyclohexane were filtered and identified as the acylurea by-product. The cyclohexane solution was concentrated to 5 ml and diluted with 5 ml of heptane to give 0.84 g (mp 95°–97° C., 54% yield) of the desired acylated hydroxylamine (C). The crude product was recrystallized from heptane to give analytically pure product: TLC (silica gel, ether) R$_f$0.51; IR (KBr) 1735 cm$^{-1}$ (s) (C=O), NMR (CDCl$_3$)$\delta$7.8–7.0 (m, 6, aromatic-H), 3.9 (s, 3, CH$_3$—O), 3.8 (q, 1, J=7 Hz, CH—CH$_3$), 3.5–2.3 (m, 4, CH$_2$N), 1.57 (d, 3, J=7 Hz, CH$_3$—CH) and 2.0=0.9 (m, 6, CH$_2$).

Anal. Calcd for C$_{19}$H$_{23}$NO$_3$: C, 72.81; H, 7.40; N, 4.47. Found: C, 73.15; H, 7.54; N, 4.58.

EXAMPLE 4

The Preparation of
N-[1-(4'-Chlorobenzoyl)-5-Methoxy-2-Methyl-3-Indolylacetyloxy]piperidine (D).

To 2.15 g (0.021 mol) of N-hydroxypiperidine dissolved in 125 ml of ether was added 3.75 g (0.01 mol) of indomethacin acid chloride (A). The reaction mixture was stirred at room temperature for 0.5 hour, then it was filtered. The residue was extracted with 75 ml of boiling heptane while the ether filtrate was evaporated to dryness. The residue from the ether filtrate was also crystallized from heptane. Together, the heptane crystallizations afforded 2.86 g (mp 130°–132° C., 65% yield) of the desired compound (D): TLC (silica gel, ether) R$_f$ 0.40; IR (KBr) 1740 and 1665 cm$^{-1}$ (s) (C=O); NMR (CDCl$_3$)$\delta$7.51 (AB quartet, 4, J=9 Hz, $\Delta_{84 AB}$=12 Hz, aromatic-H), 7.0–6.5 (m, 3, aromatic-H), 3.83 (s, 3, CH$_3$—O), 3.63 (s, 2, CH$_2$—CO$_2$), 3.6–2.4 (m, 4, CH$_2$—N), 2.38 (s, 3, CH$_3$—C=C), 2.2–1.0 (m, 6, CH$_2$).

Anal. Calcd for C$_{24}$H$_{25}$ClN$_2$O$_4$: C, 65.37; H, 5.72; N, 6.36. Found: C, 65.57; H, 5.67; N, 6.21.

EXAMPLE 5

The Preparation of
N-[2-(Acetyloxy)benzoyloxy]-N,N-Diethylamine (E)

To 9.1 g (0.0455 mol) of aspirin chloride dissolved in 100 ml of ether was added 8.1 g (0.09 mol) of N,N-diethylhydroxylamine dissolved in 100 ml of ether. The resulting suspension was filtered and the filtrate was diluted with 800 ml of heptane and filtered again. The ether-heptane filtrate was then concentrated in vacuo to give the desired compound (E) as a light yellow oil in 84% yield: TLC (silica gel, ehter) R$_f$=0.39; IR (neat) broad band 1760–1730 cm$^{-1}$ (s) (C=O); NMR (CDCl$_1$)$\delta$8.1–7.0 (m, 4, aromatic-H), 3.0 (q, 4, J=7 Hz, CH$_3$CH$_2$—N), 2.33 (s, 3, CH$_3$C—O$_2$) and 1.18 (t, 6, J=7 Hz, CH$_3$CH$_2$—N).

Anal. Calcd for C$_{13}$H$_{17}$NO$_4$: C, 62.13; H, 6.82; N, 5.58. Found: C, 62.07; H, 6.79; N, 5.28.

In similar fashion, the other compounds of the present invention can be prepared with similar success by merely following the preceding examples and substituting the appropriate generically and/or specifically described reactants and/or operating conditions of this invention for those of the preceding examples. Thus, the following additional compounds can be prepared by following the above reaction scheme:

COMPOUNDS OF FORMULA I

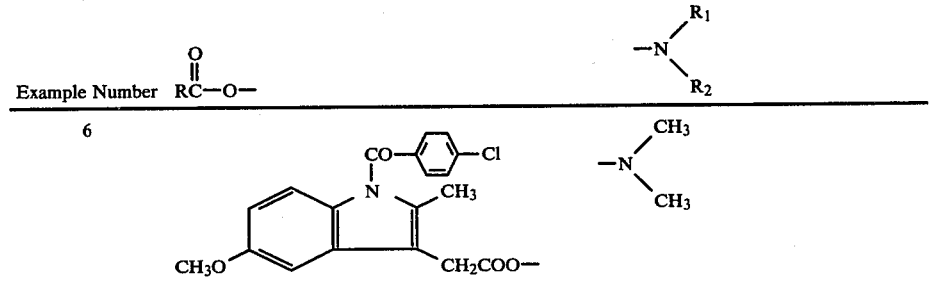

-continued
COMPOUNDS OF FORMULA I

| Example Number | $R\underset{\underset{O}{\|}}{C}-O-$ | $-N\diagup^{R_1}_{\diagdown R_2}$ |
|---|---|---|
| 7 | 1-(4-chlorobenzoyl)-5-methoxy-2-methylindol-3-yl-CH₂COO— | $-N(C_5H_{11})_2$ |
| 8 | 1-(4-chlorobenzoyl)-5-methoxy-2-methylindol-3-yl-CH₂COO— | $-N(C_8H_{17})_2$ |
| 9 | [5-fluoro-2-methyl-1-(4-methylsulfinylbenzylidene)inden-3-yl]-CH₂COO— | piperidino |
| 10 | [5-fluoro-2-methyl-1-(4-methylsulfinylbenzylidene)inden-3-yl]-CH₂COO— | —N(C₆H₅)(CH₂C₆H₅) |
| 11 | [5-fluoro-2-methyl-1-(4-methylsulfinylbenzylidene)inden-3-yl]-CH₂COO— | morpholino |
| 12 | [5-fluoro-2-methyl-1-(4-methylsulfinylbenzylidene)inden-3-yl]-CH₂COO— | imidazol-1-yl |
| 13 | 2-(6-methoxynaphth-2-yl)propanoyloxy— | $-N(CH_3)_2$ |

-continued

COMPOUNDS OF FORMULA I

| Example Number | $R\overset{O}{\underset{\phantom{O}}{C}}-O-$ | $-N\begin{subarray}{l}R_1\\ R_2\end{subarray}$ |
|---|---|---|
| 14 | 6-methoxy-naphthyl-CH(CH$_3$)COO— | —N(C$_2$H$_5$)$_2$ |
| 15 | 6-methoxy-naphthyl-CH(CH$_3$)COO— | —N(C$_5$H$_{11}$)$_2$ |
| 16 | 6-methoxy-naphthyl-CH(CH$_3$)COO— | —N(C$_8$H$_{17}$)$_2$ |
| 17 | 3-phenoxyphenyl-CH(CH$_3$)COO— | —N(piperidinyl) |
| 18 | 3-phenoxyphenyl-CH(CH$_3$)COO— | —N(C$_6$H$_5$)(CH$_2$C$_6$H$_5$) |
| 19 | 3-phenoxyphenyl-CH(CH$_3$)COO— | —N(morpholinyl) |
| 20 | 3-phenoxyphenyl-CH(CH$_3$)COO— | —N(imidazolyl) |
| 21 | 2-(CH$_3$COO)-C$_6$H$_4$-COO— | —N(CH$_3$)$_2$ |
| 22 | 2-(CH$_3$COO)-C$_6$H$_4$-COO— | —N(C$_5$H$_{11}$)$_2$ |
| 23 | 2-(CH$_3$COO)-C$_6$H$_4$-COO— | —N(C$_8$H$_{17}$)$_2$ |

-continued

COMPOUNDS OF FORMULA I

| Example Number | $RC(=O)-O-$ | $-NR_1R_2$ |
|---|---|---|
| 24 | $(CH_3)_2CHCH_2$-C$_6$H$_4$-CH(CH$_3$)COO- | piperidino |
| 25 | $(CH_3)_2CHCH_2$-C$_6$H$_4$-CH(CH$_3$)COO- | N(phenyl)(CH$_2$-phenyl) |
| 26 | $(CH_3)_2CHCH_2$-C$_6$H$_4$-CH(CH$_3$)COO- | morpholino |
| 27 | $(CH_3)_2CHCH_2$-C$_6$H$_4$-CH(CH$_3$)COO- | imidazol-1-yl |
| 28 | 1-methyl-5-(p-toluoyl)pyrrol-2-yl-CH$_2$COO- | $-N(CH_3)_2$ |
| 29 | 1-methyl-5-(p-toluoyl)pyrrol-2-yl-CH$_2$COO- | $-N(C_2H_5)_2$ |
| 30 | 1-methyl-5-(p-toluoyl)pyrrol-2-yl-CH$_2$COO- | $-N(C_5H_{11})_2$ |
| 31 | 1-methyl-5-(p-toluoyl)pyrrol-2-yl-CH$_2$COO- | $-N(C_8H_{17})_2$ |
| 32 | 2',4'-difluoro-4-hydroxy-[1,1'-biphenyl]-3-COO- | piperidino |
| 33 | 2',4'-difluoro-4-hydroxy-[1,1'-biphenyl]-3-COO- | N(phenyl)(CH$_2$-phenyl) |
| 34 | 2',4'-difluoro-4-hydroxy-[1,1'-biphenyl]-3-COO- | morpholino |

-continued

COMPOUNDS OF FORMULA I

| Example Number | RC(O)—O— | —NR₁R₂ |
|---|---|---|
| 35 | 2,4-difluoro-biphenyl with COO— and OH substituents | imidazol-1-yl |
| 36 | 2-fluorobiphenyl-4-yl-CH(CH₃)COO— | —N(CH₃)₂ |
| 37 | 2-fluorobiphenyl-4-yl-CH(CH₃)COO— | —N(C₂H₅)₂ |
| 38 | 2-fluorobiphenyl-4-yl-CH(CH₃)COO— | —N(C₅H₁₁)₂ |
| 39 | 2-fluorobiphenyl-4-yl-CH(CH₃)COO— | —N(C₈H₁₇)₂ |
| 40 | 1-oxo-2-isoindolinyl-phenyl-CH(CH₃)COO— | piperidin-1-yl |
| 41 | 1-oxo-2-isoindolinyl-phenyl-CH(CH₃)COO— | —N(C₆H₅)(CH₂C₆H₅) |
| 42 | 1-oxo-2-isoindolinyl-phenyl-CH(CH₃)COO— | morpholin-4-yl |
| 43 | 1-oxo-2-isoindolinyl-phenyl-CH(CH₃)COO— | imidazol-1-yl |
| 44 | 2-(2,3-dimethylphenylamino)benzoyloxy— | —N(CH₃)₂ |

-continued

COMPOUNDS OF FORMULA I

| Example Number | $RC(=O)-O-$ | $-N(R_1)(R_2)$ |
|---|---|---|
| 45 | 2-(2,3-dimethylphenylamino)benzoate | $-N(C_2H_5)_2$ |
| 46 | 2-(2,3-dimethylphenylamino)benzoate | $-N(C_5H_{11})_2$ |
| 47 | 2-(2,3-dimethylphenylamino)benzoate | $-N(C_8H_{17})_2$ |
| 48 | (Z)-3-[(4-chlorobenzoyl)imino]-2-(methylthio)propenoate (CH₂COO−, with S−C(4-ClC₆H₄)=N−) | piperidino |
| 49 | 2-(3-benzoylphenyl)propanoate (α-methyl, CHCOO−) | 4-methylpiperazino |
| 50 | 3-chloro-4-(allyloxy)phenylacetate (CH₂=CHCH₂O−, CH₂COO−) | pyrrolidino (−N with CH₂CH₂CH₂–CH₂CH₂CH₂) |
| 51 | 4-(2-chloro-6-cyclohexylphenyl)-4-oxobutanoate (COCH₂CH₂COO−) | 4-phenylpiperidino |
| 52 | 2-(2,6-dichloro-3-trifluoromethylphenylamino)benzoate | 4-benzylpiperidino |
| 53 | 2-(3-trifluoromethylphenylamino)benzoate | 4-phenylpiperazino |

-continued

COMPOUNDS OF FORMULA I

| Example Number | RC(O)O— | —N(R₁)(R₂) |
|---|---|---|
| 54 | 2-phenylquinoline-4-carboxylate (quinoline with 2-phenyl substituent and 4-COO—) | pyrazol-1-yl (—N linked to pyrazole) |
| 55 | 2-(2,6-dichlorophenylamino)phenylacetate [Cl-substituted phenyl-NH-phenyl-CH₂COO—] | —N(C₂H₅)₂ |
| 56 | {1-cinnamoyl-5-methoxy-2-methylindol-3-yl}acetate (indomethacin-type: CH₃O-indole with N-COCH=CH-phenyl, 2-CH₃, 3-CH₂COO—) | piperidin-1-yl |
| 57 | 4-isobutylphenylacetate [(CH₃)₂CHCH₂–C₆H₄–CH₂COO—] | —N(CH₃)₂ |
| 58 | β-(dibenzofuran-2-yl)-β-oxo-propionate [dibenzofuran–C(O)CH₂CH₂COO—] | —N(CH₃)₂ |
| 59 | 2-(2,4-dichlorophenoxy)phenylacetate [2,4-Cl₂–C₆H₃–O–C₆H₄–CH₂COO—] | —N(C₅H₁₁)₂ |
| 60 | (2-propyl-hexahydropyrano[3,4-b]indol-1-yl)acetate (indole-pyran fused, C₃H₇ substituent, CH₂COO—) | —N(C₈H₁₇)₂ |
| 61 | 2-[3-chloro-4-(pyrrolidin-1-yl)phenyl]propionate [pyrrolidine–N–C₆H₃(Cl)–CH(CH₃)–COO—] | piperidin-1-yl |
| 62 | 4-(furan)propionate with diphenyl substituents [diphenyl-substituted furan–CH₂CH₂COO—] | —N(C₆H₅)(CH₂C₆H₅) |
| 63 | 2-[(3-chloro-2-methylphenyl)amino]pyridine-3-carboxylate [pyridine-NH-C₆H₃(CH₃)(Cl), 3-COO—] | morpholin-4-yl |

-continued
COMPOUNDS OF FORMULA I

| Example Number | O<br>∥<br>RC—O— | —N⟨R₁/R₂ |
|---|---|---|
| 64 | 4-F-biphenyl-CH(CH₃)—COO— | imidazolyl (—N⟨N=CH-CH=) |
| 65 | 2-[[2-(trifluoromethyl)phenyl]thio]-N-H-phenyl with COO— | —N(C₂H₅)₂ |

EXAMPLE 66

Comparison of Effect of a Compound of Formula (I) and the Corresponding Non-Steroidal Anti-Inflammatory Agent on Inflammation A modification of the method of Tonelli et al, *Endocrinology*, 77, 625 (1965), was used. Sprague-Drawley rats were used which had a weight of 55±5 gm. The rats were first anesthesized with phenobarbitol, then the rats' right ear was burned on both sides for 10 seconds between two vertically oriented brass cylinders heated with water at 51.7° C. from a constant temperature bath. The pressure of the cylinder on the rat ear was reproduced by using only the weight of the top brass cylinder (2.5 lbs) to aplly the pressure. The burned rat ear was then immediately treated on both sides with 50 ml of vehicle (isopropyl myristate) or 0.03 M test compound in the vehicle. After 16 hours, both ears of the rat were removed along anatomical guidelines and weighed.

The increase of weight caused by the burn was determined by subtracting the weight of the untreated left ear from the weight of the treated right ear.

The percent inhibition of inflammation was then calculated according to the equation $$(WI_V - WI_T)/WI_V \times 100$$

where $WI_V$ is the weight increase of burned rat ears treated only with vehicle and $WI_T$ is the weight increase of burned rat ears treated with vehicle containing the test compound. The results for 10 rats are shown in Table I.

TABLE I

| COMPOUND | % INHIBITION |
|---|---|
| 1-(4'-Chlorobenzoyl)-5-methoxy-2-methyl-3-3-indolylacetic acid | 22.8 |
| N-[1-(4'-Chlorobenzoyl)-5-methoxy-2-methyl-3-indolylacetyloxy]-N,N-diethylamine | 50.2 |

The compounds of the present invention are conveniently administered to warm-blooded animals via conventional oral or topical administration with any suitable nontoxic pharmaceutically acceptable oral or topical inert carrier material. Such carrier materials are well known to those skilled in the art of oral and topical pharmaceutical formulations. For those not skilled in the art, reference is made to the text entitled, "REMINGTON'S PHARMACEUTICAL SCIENCES" (Fourteenth Edition), 1970. In a typical preparation for oral administration, e.g., tablet or capsule, any one of the compounds of the instant invention is combined in an anti-inflammatory effective amount with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars, such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alaginic acid, guar gum, citris pulp, carboxymethylcellulose and sodium lauryl sulfate. If desired a conventionally pharamceutically acceptable dye can be incorporated into the dosage unit form, i.e, any of the standard FD&C dyes.

Similarly, in a typical formulation for topical application, any one of the compounds of the instant invention is combined with triacetin, such that the active ingredient is present in an anti-inflammatory effective amount. The preparation is simply applied topically to the inflamed area, whereby the therapeutically active compound is dermally absorbed and "cleaved" to release the parent moiety at the site of inflammation.

Naturally, therapeutic dosage range for the compounds of the instant invention will vary with the size and needs of the patient. However, generally speaking, the following dosage guidelines will suffice. On an oral basis, the therapeutic dose required for a compound of the instant invention will generally, on a molecular basis, mimic that for the parent conventional non-steroidal moiety (e.g., indomethacin, aspirin, naproxen, etc.). On a topical basis, application of an 0.01% to 2.5% concentration of a compound of the instant invention (in a suitable topical carrier material) to the site of inflammation should suffice.

From the foregoing description, one of ordinary skill in the art can easily ascertain the essential characteristics of the instant invention, and without departing from the spirit and scope thereof, can make various changes and/or modifications of the instant invention to adapt it to various usages and conditions. As such, these changes and/or modifications are properly, equitably and intended to be, within the full range of equivalence of the following claims.

What we claim is:

1. A compound having the structural formula:

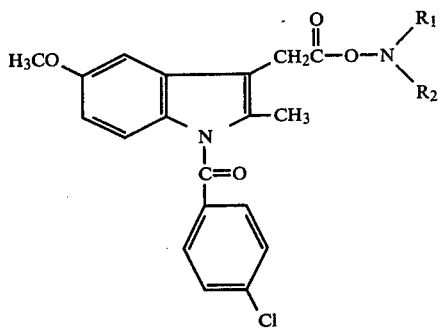

wherein $R_1$ and $R^2$, which can be the same or different, each represent a member selected from the group consisting of $C_1$–$C_8$ alkyl, $C_2$–$C_8$ alkenyl, aryl having from 6 to 10 carbons, aralkyl wherein the alkyl moiety has from 1 to 6 carbons and the aryl moiety is as above defined, $C_5$–$C_6$ cycloalkyl and $C_5$–$C_6$ cycloalkenyl, and a nontoxic pharmaceutically acceptable acid addition salt thereof.

2. The compound of claim 1, wherein $R_1$ and $R_2$ are each $C_1$–$C_8$ alkyl.

3. The compound of claim 1, wherein at least one of $R_1$ or $R_2$ is aryl.

4. The compound of claim 1, wherein at least one of $R_1$ or $R_2$ is $C_1$–$C_8$ alkyl.

5. The compound of claim 1, wherein at least one of $R_1$ or $R_2$ is aralkyl.

6. The compound of claim 1, wherein at least one of $R_1$ or $R_2$ is $C_2$–$C_8$ alkenyl.

7. The compound of claim 1 which is N-[1-(4'-chlorobenzoyl)-5-methoxy-2-methyl-3-indolylacetyloxy]-N,N-dimethylamine.

8. The compound of claim 1 which is N-[1-(4'-chlorobenzoyl)-5-methoxy-2-methyl-3-indolylacetyloxy]-N,N-diethylamine.

9. The compound of claim 1 which is N-[1-(4'-chlorobenzoyl)-5-methoxy-2-methyl-3-indolylacetyloxy]-N,N-dipentylamine.

10. The compound of claim 1 which is N-[1-(4'-chlorobenzoyl)-5-methoxy-2-methyl-3-indolylacetyloxy]-N,N-dioctylamine.

11. A method for alleviating inflammation in or on a warm-blooded animal exhibiting an inflammatory response which comprises administering thereto an antiinflammatory effective amount of a compound as defined in claim 1.

* * * * *